(12) United States Patent
Terashita et al.

(10) Patent No.: US 7,582,662 B2
(45) Date of Patent: Sep. 1, 2009

(54) BODY WEIGHT GAIN INHIBITOR

(75) Inventors: Zen-ichi Terashita, Osaka (JP); Keiji Kusumoto, Osaka (JP); Fuminari Yamaguchi, Osaka (JP); Yoshimi Imura, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 533 days.

(21) Appl. No.: 10/540,369

(22) PCT Filed: Dec. 25, 2003

(86) PCT No.: PCT/JP03/16656

§ 371 (c)(1),
(2), (4) Date: Jun. 23, 2005

(87) PCT Pub. No.: WO2004/060399

PCT Pub. Date: Jul. 22, 2004

(65) Prior Publication Data

US 2006/0069133 A1 Mar. 30, 2006

(30) Foreign Application Priority Data

Dec. 27, 2002 (JP) ............................. 2002-380386

(51) Int. Cl.
*A61K 31/4245* (2006.01)
(52) U.S. Cl. .................................................. 514/364
(58) Field of Classification Search ............. None
See application file for complete search history.

(56) References Cited

U.S. PATENT DOCUMENTS

| 6,107,323 | A | 8/2000 | Tamura et al. |
| 6,177,587 | B1 | 1/2001 | Hashimoto et al. |
| 6,251,926 | B1 * | 6/2001 | Momose et al. ............. 514/364 |
| 2003/0055039 | A1 | 3/2003 | Ikeya et al. |
| 2003/0068374 | A1 | 4/2003 | Kamel et al. |
| 2003/0083342 | A1 | 5/2003 | Steele |
| 2003/0187038 | A1 | 10/2003 | Imura et al. |
| 2004/0023840 | A1 | 2/2004 | Gasparo et al. |
| 2004/0034065 | A1 | 2/2004 | Allison et al. |
| 2005/0032854 | A1 | 2/2005 | Kawahara et al. |

FOREIGN PATENT DOCUMENTS

| EP | 1304121 A1 | 4/2003 |
| JP | 11-43474 | 2/1999 |
| WO | WO 01/05428 | 1/2001 |
| WO | WO 01/60362 | 8/2001 |
| WO | WO 01/60410 | 8/2001 |
| WO | WO 01/76573 | 10/2001 |
| WO | WO 01/76574 | 10/2001 |
| WO | WO 02/15933 | 2/2002 |
| WO | WO 02/15935 | 2/2002 |
| WO | WO 02/074340 | 9/2002 |
| WO | WO 03/013609 | 2/2003 |
| WO | WO 03/047573 | 6/2003 |

OTHER PUBLICATIONS

Ortlepp, J., et al., "Angiotensin II Receptor Antagonism and ACE Inhibition Ameliorate Hyperinsulinema and Obesity in a Murine Model of Polygenic Obesity", *Journal of the American College of Cardiology*, (2002), vol. 39, No. 5, Supplement A, p. 232A.

Noda, M., et al., "Involvement of Angiotensin II in Progression of Renal Injury in Rats with Genetic Non-Insulin-Dependent Diabetes Mellitus (Wistar Fatty Rats)", *Japan J. Pharmacol.*, (2001), vol. 85, pp. 416-422.

* cited by examiner

*Primary Examiner*—Laura L. Stockton
(74) *Attorney, Agent, or Firm*—Finnegan, Henderson, Farabow, Garrett & Dunner, LLP

(57) ABSTRACT

The invention provides a pharmaceutical agent containing a compound having an angiotensin II antagonistic activity, a prodrug thereof or a salt thereof, which shows superior effect for the suppression of body weight gain. In addition, the present invention provides such a pharmaceutical agent as does not increase body weights of patients even if a therapeutically effective PPARγ agonistic substance is administered in the treatment of diabetes and other diseases.

2 Claims, No Drawings

US 7,582,662 B2

BODY WEIGHT GAIN INHIBITOR

This application is the National Phase filing of International Patent Application No. PCT/JP2003/016656, filed Dec. 25, 2003.

TECHNICAL FIELD

The present invention relates to a body weight gain inhibitor, particularly an inhibitor of body weight gain induced by a PPARγ agonist-like substance, which is useful for the treatment of diabetes and the like.

BACKGROUND ART

In view of the fact that becoming obese due to body weight gain is not only undesirable for cosmetic reasons but also poses a greater risk for health that leads to life-style related diseases such as diabetes, hypertension, hyperlipidemia and the like; suppression of body weight gain is considered to be important for reducing the incidence of life-style related diseases. While suppression of body weight gain naturally requires sufficient exercise and balanced dietary habits, these alone are practically insufficient to achieve the goal and, as the situation stands, a method of appropriately controlling the body weight is not easy to find.

On the other hand, body weight gain of patients suffering from life-style related diseases such as diabetes, hypertension, hyperlipidemia and the like often causes aggravation of the illness. Since body weight gain is caused not only by way of ingestion of food but also sometimes by the administration of therapeutic agents for life-style related diseases, suppression of body weight gain of patients is also significant for the treatment of life-style related diseases such as diabetes, hypertension, hyperlipidemia and the like.

It has been known that insulin sensitizers recognized as highly superior therapeutic agents for diabetes (e.g., troglitazone, pioglitazone, rosiglitazone etc.) have a PPARγ agonistic activity (e.g., Journal of Pharmacology and Experimental Therapeutics, 284, 751-759 (1998)). While these pharmaceutical agents are effective for the treatment of diabetes, some of them have been found to increase body weights of patients after their administration (WO 93/03724, Diabetes, 47, suppl. 1, A18, No. 69, 1998). Such drug-induced body weight gain is one of the effects desired to be avoided as much as possible for patients with diabetes. This is because obesity causes aggravation of diabetes.

For example, JP-A 5-271228, JP-A 2001-316296 and the like describe that a compound having an angiotensin II antagonistic activity shows a superior therapeutic effect for circulatory diseases and the like, such as hypertension, cardiac diseases, stroke, renal diseases, arteriosclerosis and the like. In addition, JP-A 9-323940 describes that a pharmaceutical agent comprising a compound having an angiotensin II antagonistic activity in combination with a compound having an insulin sensitizing activity and the like can markedly decrease the dose of each active ingredient as compared to the dose thereof used as a single agent, which in turn can decrease expression of side effects as compared to the use of the active ingredients as single agents, and can be advantageously used as a prophylactic or therapeutic agent for various angiotensin II-mediated diseases, particularly, as a prophylactic or therapeutic agent for arterial hypertension associated with arteriosclerosis or hypertension as a complication and the like.

JP-A 2001-316296 describes obesity, which is one of the metabolic/nutritional disturbances, as a target disease of a compound having an angiotensin II antagonistic activity. However, this publication does not report on the suppression of body weight gain (particularly, body weight gain induced by a PPARγ agonist-like substance) by a compound having an angiotensin II antagonistic activity, irrespective of whether excess weight (including obesity) is observed.

OBJECT OF INVENTION

The present invention aims at providing a pharmaceutical agent exhibiting a superior effect on the suppression of body weight gain.

In addition, the present invention aims at providing such a pharmaceutical agent as does not increase body weights of patients even if a therapeutically effective PPARγ agonistic substance is administered in the treatment of diabetes and other diseases.

SUMMARY OF THE INVENTION

The present inventors have first found that a compound having an angiotensin II antagonistic activity, a prodrug thereof or a salt thereof (hereinafter sometimes to be simply abbreviated as a "compound having an angiotensin II antagonistic acyivity") suppresses body weight gain, which resulted in the completion of the present invention.

Accordingly, the present invention relates to:

(1) a body weight gain inhibitor comprising a compound having an angiotensin II antagonistic activity, a prodrug thereof or a salt thereof, (2) the inhibitor according to the above-mentioned (1), wherein the body weight gain occurs before reaching obesity, (3) the inhibitor according to the above-mentioned (1), wherein the body weight gain is observed in a patient with obesity, (4) the inhibitor according to the above-mentioned (3), wherein the obesity is associated with diabetes, (5) the inhibitor according to the above-mentioned (4), further comprising a PPARγ agonist-like substance in combination, (6) the inhibitor according to the above-mentioned (1), wherein the body weight gain is induced by a PPARγ agonist-like substance, (7) the inhibitor according to the above-mentioned (6), which suppresses the body weight gain induced by a PPARγ agonist-like substance to not more than about 80%, (8) the inhibitor according to the above-mentioned (1), wherein the compound having an angiotensin II antagonistic activity is a non-peptidic compound, (9) the inhibitor according to the above-mentioned (1), wherein the compound having an angiotensin II antagonistic activity has an oxygen atom in a molecule,

(10) the inhibitor according to the above-mentioned (1), wherein the compound having an angiotensin II antagonistic activity has an ether bond or a carbonyl group in a molecule,

(11) the inhibitor according to the above-mentioned (1), wherein the compound having an angiotensin II antagonistic activity is a compound represented by the formula (I):

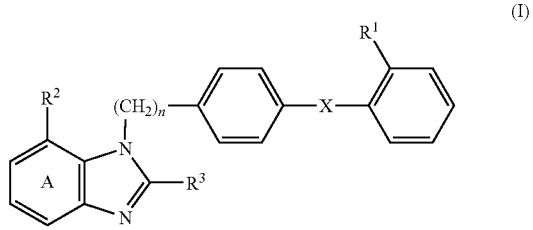

wherein R¹ denotes a group which can form an anion or a group which can be converted into the group which can form an anion, X denotes that the phenylene group and the phenyl group are bound directly or through a spacer having no more than 2 of atom chains, n denotes 1 or 2, a ring A denotes a benzene ring optionally further having a substituent, R² denotes a group which can form an anion or a group which can be converted into the group which can form an anion, and R³ denotes a hydrocarbon residue which may be bound via a hetero atom and which may have a substituent,

(12) the inhibitor according to the above-mentioned (1), wherein the compound having an angiotensin II antagonistic activity is 2-ethoxy-1-[[2'-(5-oxo-2,5-dihydro-1,2,4-oxadiazol-3-yl)biphenyl-4-yl]methyl]-1H-benzimidazole-7-carboxylic acid,

(13) the inhibitor according to the above-mentioned (1), wherein the compound having an angiotensin II antagonistic activity, or a salt thereof is Losartan, Losartan potassium, Eprosartan, Candesartan cilexetil, Candesartan, Valsartan, Telmisartan, Irbesartan, Olmesartan, Olmesartan medoxomil, or Tasosartan,

(14) a method of inhibiting a body weight gain in a mammal, which comprises administering an effective amount of a compound having an angiotensin II antagonistic activity, a prodrug thereof or a salt thereof to the mammal,

(15) use of a compound having an angiotensin II antagonistic activity, a prodrug thereof or a salt thereof for the production of a body weight gain inhibitor, and the like.

The angiotensin II antagonistic activity in the present invention is inhibiting binding of angiotensin II with an angiotensin II receptor on a cell membrane competitively or non-competitively. Compounds having such an angiotensin II antagonistic activity are known to have an action to attenuate the strong vasoconstrictive action and vascular smooth muscle growth action induced by angiotensin II, and alleviate symptoms of hypertension.

A compound having an angiotensin II antagonistic activity used in the preset invention may be peptidic or non-peptidic, and a compound such as a non-peptidic compound having the antagonistic activity which is advantageous in, for example, long acting time is preferable. As a compound having the angiotensin II antagonistic activity, a compound having an oxygen atom in its molecule is preferable and, inter alia, a compound such as a compound having an ether linkage or a carbonyl group (the carbonyl group may form a hydroxyl group by resonance) is preferable, a compound such as a compound having an ether linkage or a ketone derivative is more preferable and, inter alia, a compound such as an ether derivative is preferable.

As a non-peptidic compound having angiotensin II antagonistic activity, imidazole derivatives are disclosed in JP-A 56-71073, JP-A 56-71074, JP-A 57-98270, JP-A 58-157768, U.S. Pat. No. 4,355,040, U.S. Pat. No. 4,340,598 etc., improved imidazole derivatives are disclosed in EP-253310, EP-291969, EP-324377, EP-403158, WO-9100277, JP-A 63-23868, JP-A 1-117876 etc., pyrrole, pyrazole and triazole derivatives are disclosed in U.S. Pat. No. 5,183,899, EP-323841, EP-409332, JP-A 1-287071 etc., benzimidazole derivative are disclosed in U.S. Pat. No. 4,880,804, EP-0392317, EP-0399732, EP-0400835, EP-425921, EP-459136, JP-A 3-63264 etc., azaindene derivatives are disclosed in EP-399731 etc., pyrimidone derivatives are disclosed in EP-407342 etc., quinazoline derivatives are disclosed in EP-411766 etc., xanthine derivatives are disclosed in EP-430300 etc., fused imidazole derivatives are disclosed in EP-434038 etc., pyrimidinedione derivatives are disclosed in EP-442473 etc., thienopyridone derivatives are disclosed in EP-443568 etc., and heterocyclic compounds are disclosed in EP-445811, EP-483683, EP-518033, EP-520423, EP-588299, EP-603712 etc. Representative compounds of the above compounds are described in *Journal of Medicinal Chemistry*, (Vol. 39, No. 3, pp 625-656, 1996). As a non-peptidic compound having angiotensin II antagonistic activity, in addition to the aforementioned compounds described in the known literature, any compounds may be used as long as they are non-peptidic compounds having the angiotensin II antagonistic activity, inter alia, Losartan (DuP753), Losartan potassium, Eprosartan (SK&F108566), Candesartan cilexetil (TCV-116), Valsartan (CGP-48933), Telmisartan (BIBR277), Irbesartan (SR47436), Tasosartan (ANA-756), Olmesartan medoxomil and active metabolites thereof (Candesartan, Olmesartan etc.) are preferably used.

In addition, as a non-peptidic compound having the angiotensin II antagonistic activity, for example, a benzimidazole derivative represented by the formula (I):

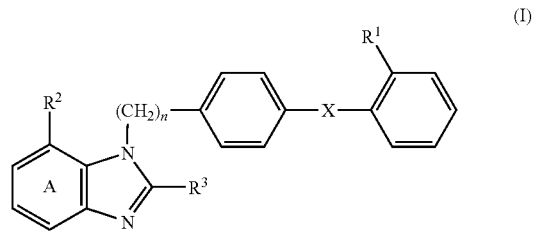

wherein R¹ denotes a group which can form an anion or a group which can be converted into the group which can form an anion, X denotes that a phenylene group and a phenyl group are bound directly or via a spacer having no more than 2 of atom chains, n denotes an integer of 1 or 2, a ring A denotes a benzene ring optionally further having a substituent, R² denotes a group which can form an anion or a group which can be converted into the group which can form an anion, and R³ denotes a hydrocarbon residue which may be bound via a hetero atom and may have a substituent (preferably hydrocarbon residue which may have a substituent and is bound via an oxygen atom) or a salt thereof is preferably used.

In the above formula (I), examples of a group which can form an anion (a group having a hydrogen atom which can be liberated as a proton) as R¹ include (1) a carboxyl group, (2) a tetrazolyl group, (3) a trifluoromethanesulfonic acid amide group ($-NHSO_2CF_3$), (4) a phosphoric acid group, (5) a sulfonic acid group, and (6) 5 to 7-membered (preferably 5 to 6-membered) monocyclic optionally substituted heterocyclic residue containing 1 or 2 or more of N, S or O.

Examples of the "5 to 7-membered (preferably 5 to 6-membered) monocyclic optionally substituted heterocyclic residue containing 1 or 2 or more of N, S or O" include

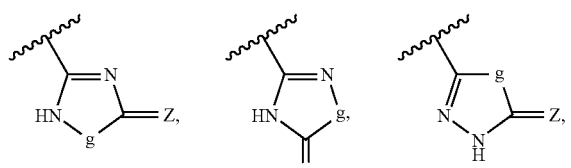
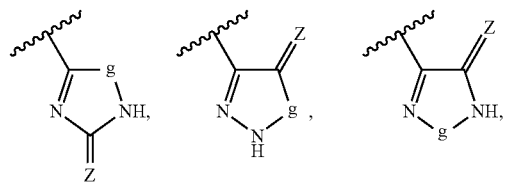
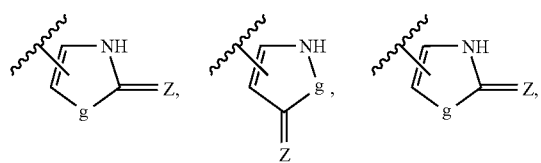
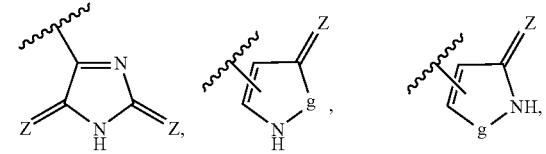
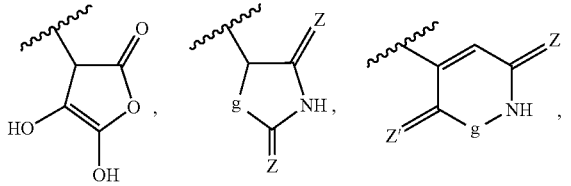
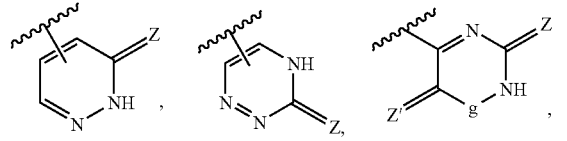
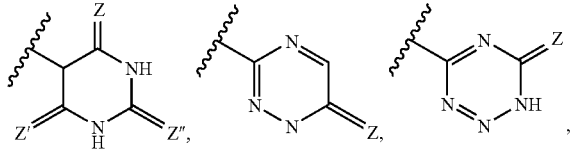
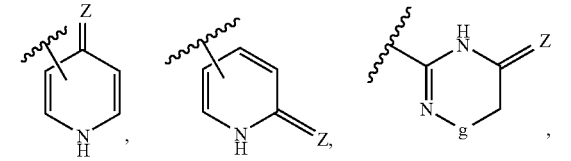
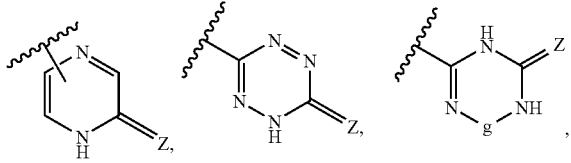
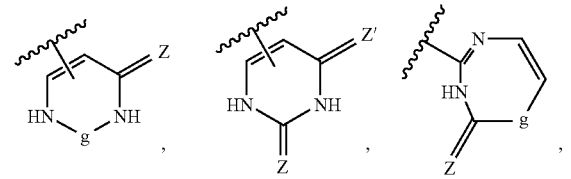

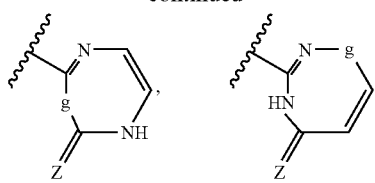

etc. The bond between the heterocyclic residue represented by $R^1$ and the phenyl group to be bound with the heterocyclic residue includes not only the aforementioned carbon-carbon binding but also binding via one of a plurality of nitrogen atoms when g in the above formula denotes —NH— or the like. For example, when $R^1$ is represented by

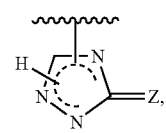

specifically, there are

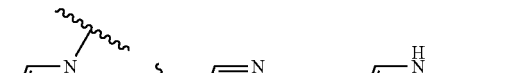

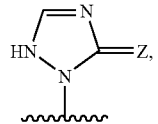

respectively. Other examples of binding via a nitrogen atom include

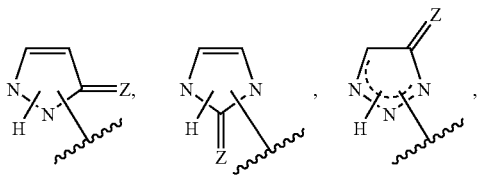

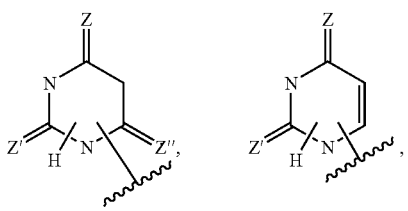

-continued

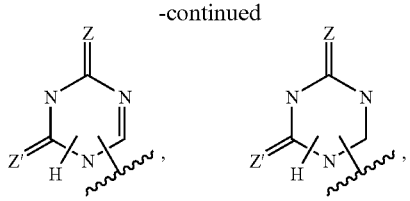

etc.

In the above formula, g denotes —CH$_2$—, —NH—, —O— or —S(O)$_m$—, >=Z, >=Z' and >=Z" denote a carbonyl group, a thiocarbonyl group or an optionally oxidized sulfur atom (e.g., S, S(O), S(O)$_2$ etc.) (preferably carbonyl or thiocarbonyl group, more preferably carbonyl group), and m denotes an integer of 0, 1 or 2.

As a heterocyclic residue represented by $R^1$, for example, a group having an —NH— group or an —OH group as a proton donor and a carbonyl group, a thiocarbonyl group, a sulfinyl group or the like as a proton acceptor at the same time, such as an oxadiazolone ring, an oxadiazolothione ring or a thiadiazolone ring is preferable. In addition, a heterocyclic residue denoted by $R^1$ may form a fused ring by binding with a cyclic substituent and, as a heterocyclic residue represented by $R^1$, 5 or 6-membered ring residue is preferable, and 5-membered ring residue is more preferable.

As a heterocyclic residue represented by $R^1$, a group represented by the formula;

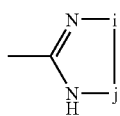

wherein i denotes —O— or —S—, j denotes >=O, >=S or >=S(O)$_m$, and m is as defined above (inter alia, 2,5-dihydro-5-oxo-1,2,4-oxadiazol-3-yl, 2,5-dihydro-5-thioxo-1,2,4-oxadizole-3-yl, 2,5-dihydro-5-oxo-1,2,4-thiadiazole-3-yl, among them, 2,5-dihydro-5-oxo-1,2,4-oxadiazol-3-yl) is preferable.

In addition, the heterocyclic residue ($R^1$) has tautomers as described below. For example, when Z=O and g=O in

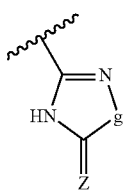

three tautomers of a', b' and c' are present as described by:

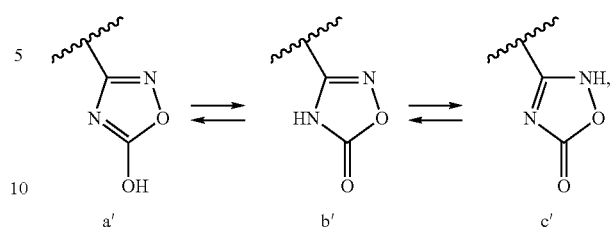

and a heterocyclic residue represented by:

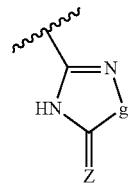

includes all of the aforementioned a', b' and c'.

A group which may form an anion as $R^1$ may be protected with a lower (C$_{1-4}$)alkyl group or an acyl group (e.g., lower (C$_{2-5}$)alkanoyl, benzoyl etc.), each group optionally being substituted at a substitutable position.

Examples of an optionally substituted lower (C$_{1-4}$)alkyl group include (1) a lower (C$_{1-4}$)alkyl group optionally substituted with 1 to 3 phenyl groups optionally having halogen atom, nitro, lower (C$_{1-4}$)alkyl, lower (C$_{1-4}$)alkoxy etc. (e.g., methyl, triphenylmethyl, p-methoxybenzyl, p-nitrobenzyl etc.), (2) a lower (C$_{1-4}$)alkoxy-lower (C$_{1-4}$)alkyl group (e.g., methoxymethyl, ethoxymethyl etc.), and (3) a group represented by the formula —CH(R$^4$)—OCOR$^5$ [wherein R$^4$ denotes (a) hydrogen, (b) a straight or branched lower alkyl group having a carbon number of 1 to 6 (e.g., methyl, ethyl, n-propyl, isopropyl, n-butyl, isobutyl, t-butyl, n-pentyl, isopentyl, neopentyl etc.), (c) a straight or branched lower alkenyl group having a carbon number of 2 to 6 or (d) a cycloalkyl group having a carbon number of 3 to 8 (e.g., cyclopentyl, cyclohexyl, cycloheptyl etc.) and R$^5$ denotes (a) a straight or branched lower alkyl group having a carbon number of 1 to 6 (e.g., methyl, ethyl, n-propyl, isopropyl, n-butyl, isobutyl, sec-butyl, t-butyl, n-pentyl, isopentyl, neopentyl etc.), (b) a straight or branched lower alkenyl group having a carbon number of 2 to 6, (c) a lower alkyl group having a carbon number of 1 to 3 substituted with a cycloalkyl group having a carbon number of 3 to 8 (e.g., cyclopentyl, cyclohexyl, cycloheptyl etc.) or an optionally substituted aryl group (e.g., phenyl or naphthyl group optionally having halogen atom, nitro, lower (C$_{1-4}$)alkyl, lower (C$_{1-4}$)alkoxy etc.) (e.g., benzyl, p-chlorobenzyl, phenethyl, cyclopentylmethyl, cyclohexylmethyl etc.), (d) a lower alkenyl group having a carbon number of 2 to 3 substituted with cycloalkyl having a carbon number of 3 to 8 or an optionally substituted aryl group (e.g., phenyl or naphthyl group optionally having halogen atom, nitro, lower (C$_{1-4}$)alkyl, lower (C$_{1-4}$)alkoxy etc.) (e.g., groups having an alkenyl part such as vinyl, propenyl, allyl, isopropenyl etc. such as cinnamyl etc.), (e) an optionally substituted aryl group (e.g., phenyl or naphthyl group optionally having halogen atom, nitro, lower (C$_{1-4}$)alkyl, lower (C$_{1-4}$)alkoxy etc. such as phenyl, p-tolyl, naphthyl etc.), (f) a straight or branched lower alkoxy group having a carbon number of 1 to 6 (e.g., methoxy, ethoxy, n-propoxy, isopropoxy, n-butoxy, isobutoxy, sec-butoxy, t-butoxy, n-pentyloxy, isopentyloxy, neopentyloxy etc.), (g) a straight or branched lower alkenyloxy group having a carbon number of 2 to 8 (e.g., allyloxy, isobutenyloxy etc.), (h) a cycloalkyloxy group having a carbon number of 3 to 8 (e.g., cyclopentyloxy, cyclohexyloxy, cycloheptyloxy etc.), (i) a lower alkoxy group having a carbon number of 1 to 3 substituted with cycloalkyl having a carbon number of 3 to 8 (e.g., cyclopentyl, cyclohexyl, cycloheptyl etc.) or an optionally substituted aryl group (e.g., phenyl or naphthyl group optionally having halogen atom, nitro, lower ($C_{1-4}$)alkyl, lower ($C_{1-4}$)alkoxy etc.) (e.g., groups having an alkoxy part such as methoxy, ethoxy, n-propoxy, isopropoxy etc. such as benzyloxy, phenethyloxy, cyclopentylmethoxy, cyclohexylmethoxy etc.), (j) a lower alkenyloxy group having a carbon number of 2 to 3 substituted with cycloalkyl having a carbon number of 3 to 8 (e.g., cyclopentyl, cyclohexyl, cycloheptyl etc.) or an optionally substituted aryl group (e.g., phenyl or naphthyl group optionally having halogen atom, nitro, lower ($C_{1-4}$)alkyl, lower ($C_{1-4}$)alkoxy etc.) (e.g., groups having an alkenyloxy part such as vinyloxy, propenyloxy, allyloxy, isopropenyloxy etc. such as cinnamyloxy etc.) or (k) an optionally substituted aryloxy group (e.g., phenoxy or naphthoxy group optionally having halogen atom, nitro, lower ($C_{1-4}$)alkyl, lower ($C_{1-4}$) alkoxy etc. such as phenoxy, p-nitrophenoxy, naphthoxy etc.)].

In addition, a group which may form an anion as $R^1$ may have a substituent such as an optionally substituted lower ($C_{1-4}$)alkyl group (examples thereof include the same "optionally substituted lower ($C_{1-4}$)alkyl group" as that exemplified as a protecting group for the aforementioned group which can form an anion as $R^1$), halogen atom, nitro, cyano, lower ($C_{1-4}$)alkoxy, and amino optionally substituted with 1 to 2 lower ($C_{1-4}$)alkyl(s), at a substitutable position, in addition to a protecting group such as the aforementioned optionally substituted lower ($C_{1-4}$)alkyl group and acyl group (e.g., lower ($C_{2-5}$)alkanoyl, benzoyl etc.).

In the aforementioned formula, a group which can be converted into a group which can form an anion (a group having a hydrogen atom which can be liberated as a proton) as $R^1$ may be a group which can be converted into a group which can form an anion under the biological, that is, physiological conditions (e.g., a reaction in a living body such as oxidation, reduction or hydrolysis by an enzyme in a living body) (so-called prodrug), or may be a group which can be converted into a group which can form an anion represented by $R^1$ by a chemical reaction (so-called synthetic intermediate) such as cyano, an N-hydroxycarbamimidoyl group (—C(=N—OH)—$NH_2$), or (1) a carboxyl group, (2) a tetrazolyl group, (3) a trifluoromethanesulfonic acid amide group (—$NHSO_2CF_3$), (4) a phosphoric acid group, (5) a sulfonic acid group, and (6) an optionally substituted 5 to 7-membered (preferably 5 or 6-membered) monocyclic heterocyclic residue containing 1 or 2 or more of N, S or O, each being protected with an optionally substituted lower ($C_{1-4}$)alkyl group or acyl group.

As $R^1$, carboxyl, tetrazolyl or 2,5-dihydro-5-oxo-1,2,4-oxadiazol-3-yl (preferably tetrazolyl) optionally protected with an optionally substituted lower ($C_{1-4}$)alkyl (e.g., methyl, triphenylmethyl, methoxymethyl, ethoxymethyl, p-methoxybenzyl, p-nitrobenzyl etc.) or an acyl group (e.g., lower ($C_{2-5}$)alkanoyl, benzoyl etc.), or cyano, or N-hydroxycarbamimidoyl (preferably cyano) is preferable and, inter alia, cyano is preferably used.

In the above formula, X denotes that adjacent phenylene group and phenyl group are bound directly or via no more than 2 of atom chains (preferably direct binding) and, as a spacer having no more than 2 of atom chains, any divalent chains in which the number of atoms constituting a straight part is 1 or 2 may be used, and the spacer may have a side chain. Specifically, lower ($C_{1-4}$)alkylene in which the number of atoms constituting a straight part is 1 or 2, —CO—, —O—, —S—, —NH—, —CO—NH—, —O—$CH_2$—, —S—$CH_2$—, —CH=CH— and the like can be mentioned.

In the above formula, n denotes an integer of 1 or 2 (preferably 1).

In the above formula, a ring A denotes a benzene ring optionally further having an substituent in addition to a substituent $R^2$, and examples of the substituent include (1) halogen (e.g., F, Cl, Br etc.), (2) cyano, (3) nitro, (4) optionally substituted lower ($C_{1-4}$)alkyl, (5) lower ($C_{1-4}$)alkoxy, (6) optionally substituted amino group (e.g., amino, N-lower ($C_{1-4}$) alkylamino (e.g., methylamino etc.), N,N-di-lower($C_{1-4}$) alkylamino (e.g., dimethylamino etc.), N-arylamino (e.g., phenylamino etc.), alicyclic amino (e.g., morpholino, piperidino, piperazino, N-phenylpiperazino etc.) etc.), (7) a group represented by the formula —CO-D' [wherein D' denotes a hydroxyl group, or lower ($C_{1-4}$)alkoxy in which the alkyl part may be substituted with hydroxyl group, lower ($C_{1-4}$)alkoxy, lower ($C_{2-6}$)alkanoyloxy (e.g., acetoxy, pivaloyloxy etc.), lower ($C_{1-6}$)alkoxycarbonyloxy (e.g., methoxycarbonyloxy, ethoxycarbonyloxy etc.) or lower ($C_{3-6}$)cycloalkoxycarbonyloxy (e.g., cyclohexyloxycarbonyloxy etc.)], (8) tetrazolyl, a trifluoromethanesulfonic acid amide group, a phosphoric acid group and a sulfonic acid group which may be protected with an optionally substituted lower ($C_{1-4}$)alkyl (examples thereof include the same "optionally substituted lower($C_{1-4}$)alkyl group" as that exemplified as a protecting group for the aforementioned group which can form an anion as $R^1$) or acyl (e.g., lower ($C_{2-5}$) alkanoyl, benzoyl etc.).

These substituents may replace 1 to 2 substitutable positions on the benzene ring at the same time and, as a substituent which is further possessed by a ring A in addition to the substituent $R^2$, an optionally substituted lower ($C_{1-4}$)alkyl (e.g., lower ($C_{1-4}$)alkyl optionally substituted with hydroxyl group, carboxyl group, halogen etc.), halogen and the like are preferable, and it is more preferable that a ring A does not have a substituent in addition to the substituent $R^2$.

In the above formula, examples of a group which can form an anion (a group having a hydrogen atom which can be liberated as a proton) as $R^2$ include (1) an optionally esterified or amidated carboxyl group, (2) a tetrazolyl group, (3) a trifluoromethanesulfonic acid amide group (—$NHSO_2CF_3$), (4) a phosphoric group, (5) a sulfonic acid group, and the like, and these groups may be protected with an optionally substituted lower alkyl group (examples thereof include the same "optionally substituted lower ($C_{1-4}$)alkyl group" as that exemplified as a protecting group for the aforementioned group which can form an anion as $R^1$) or an acyl group (e.g., lower ($C_{2-5}$)alkanoyl, benzyl etc.), and any groups may be used as long as they are a group which can form an anion or a group which can be converted into the group which can form an anion, under the biological, that is, physiological conditions (e.g., a reaction in a living body such as oxidation, reduction and hydrolysis by an enzyme in a living body) or chemically.

Examples of an optionally esterified or amidated carboxyl as $R^2$ include a group represented by the formula —CO-D [wherein D denotes (1) hydroxyl group, (2) optionally substituted amino (e.g., amino, N-lower ($C_{1-4}$)alkylamino, N,N-di-lower ($C_{1-4}$) alkylamino etc.) or (3) optionally substituted alkoxy {e.g., (i) a lower ($C_{1-6}$)alkoxy group in which the alkyl part may be substituted with hydroxyl group, optionally substituted amino (e.g., amino, N-lower ($C_{1-4}$)alkylamino, N,N-di-lower ($C_{1-4}$) alkylamino, piperidino, morpholino etc.), halogen, lower ($C_{1-4}$) alkoxy, lower ($C_{1-6}$)alkylthio, lower ($C_{3-8}$)cycloalkoxy or optionally substituted dioxolenyl (e.g., 5-methyl-2-oxo-1,3-dioxolen-4-yl etc.), or (ii) a group represented by the formula —O—CH($R^6$)—OCOR$^7$ [wherein $R^6$ denotes (a) hydrogen, (b) a straight or branched lower alkyl group having a carbon number of 1 to 6 (e.g., methyl, ethyl, n-propyl, isopropyl, n-butyl, isobutyl, t-butyl, n-pentyl, isopentyl, neopentyl etc.), (c) a straight or branched lower alkenyl group having a carbon number of 2 to 6 or (d) a cycloalkyl group having a carbon number of 3 to 8 (e.g., cyclopentyl, cyclohexyl, cycloheptyl etc.) and $R^7$ denotes (a) a straight or branched lower alkyl group having a carbon number of 1 to 6 (e.g., methyl, ethyl, n-propyl, isopropyl, n-butyl, isobutyl, sec-butyl, t-butyl, n-pentyl, isopentyl, neopentyl etc.), (b) a straight or branched lower alkenyl group having a carbon number of 2 to 6, (c) a lower alkyl group having a carbon number of 1 to 3 substituted with a cycloalkyl group having a carbon number of 3 to 8 (e.g., cyclopentyl, cyclohexyl, cycloheptyl etc.) or an optionally substituted aryl group (e.g., phenyl or naphthyl group optionally having halogen atom, nitro, lower ($C_{1-4}$)alkyl, lower ($C_{1-4}$)alkoxy etc.) (e.g., benzyl, p-chlorobenzyl, phenethyl, cyclopentylmethyl, cyclohexylmethyl etc.), (d) a lower alkenyl group having a carbon number of 2 to 3 substituted with cycloalkyl having a carbon number of 3 to 8 or optionally substituted aryl group (e.g, phenyl or naphthyl group optionally having halogen atom, nitro, lower ($C_{1-4}$)alkyl, ($C_{1-4}$) alkoxy etc.) (e.g., groups having an alkenyl part such as vinyl, propenyl, allyl, isopropenyl etc. such as cinnamyl etc.), (e) an optionally substituted aryl group (e.g., phenyl or naphthyl group optionally having halogen atom, nitro, lower ($C_{1-4}$)alkyl, lower ($C_{1-4}$)alkoxy etc. such as phenyl, p-tolyl, naphthyl etc.), (f) a straight or branched lower alkoxy group having a carbon number of 1 to 6 (e.g., methoxy, ethoxy, n-propoxy, isopropoxy, n-butoxy, isobutoxy, sec-butoxy, t-butoxy, n-pentyloxy, isopentyloxy, neopentyloxy etc.), (g) a straight or branched lower alkenyloxy group having a carbon number of 2 to 8 (e.g., allyloxy, isobutenyloxy etc,), (h) a cycloalkyloxy group having a carbon number of 3 to 8 (e.g., cyclopentyloxy, cyclohexyloxy, cycloheptyloxy etc.), (i) a lower alkoxy group having a carbon number of 1 to 3 substituted with cycloalkyl having a carbon number of 3 to 8 (e.g., cyclopentyl, cyclohexyl, cycloheptyl etc.) or an optionally substitute aryl group (e.g., phenyl or naphthyl group optionally having halogen atom, nitro, lower ($C_{1-4}$)alkyl lower, ($C_{1-4}$)alkoxy etc.) (e.g., groups having an alkoxy group such as methoxy, ethoxy, n-propoxy, isopropoxy etc. such as benzyloxy, phenethyloxy, cyclopentylmethoxy, cyclohexylmethoxy etc.) (j) a lower alkenyloxy group having a carbon number of 2 to 3 substituted with cycloalkyl having a carbon number of 3 to 8 (e.g., cyclopentyl, cyclohexyl, cycloheptyl etc.) or an optionally substituted aryl group (e.g., phenyl or naphthyl group optionally having halogen atom, nitro, lower ($C_{1-4}$)alkyl, lower ($C_{1-4}$)alkoxy etc.) (e.g., groups having an alkenyloxy part such as vinyloxy, propenyloxy, allyloxy, isopropenyloxy etc. such as cinnamyloxy etc.) or (k) an optionally substituted aryloxy group (e.g., phenoxy or naphthoxy group optionally having halogen atom, nitro, lower ($C_{1-4}$)alkyl, lower ($C_{1-4}$) alkoxy etc. such as phenoxy, p-nitrophenoxy, naphthoxy etc.)]}].

As $R^2$, optionally esterified carboxyl is preferable, and examples thereof include —COOH and a salt thereof, —COOMe, —COOEt, —COOtBu, —COOPr, pivaloyloxymethoxycarbonyl, 1-(cyclohexyloxycarbonyloxy)ethoxycarbonyl, 5-methyl-2-oxo-1,3-dioxolen-4-yl-methoxycarbonyl, acetoxymethoxycarbonyl, propionyloxymethoxycarbonyl, n-butyryloxymethoxycarbonyl, isobutyryloxymethoxycarbonyl, 1-(ethoxycarbonyloxy)ethoxycarbonyl, 1-(acetoxy)ethoxycarbonyl, 1-(isobutyryloxy)ethoxycarbonyl, cyclohexylcarbonyloxymethoxycarbonyl, benzoyloxymethoxycarbonyl, cinnamyloxycarbonyl, cyclopentylcarbonyloxymethoxycarbonyl and the like, and any groups may be used as far as they are a group which can form an anion (e.g., COO$^-$, a derivative thereof etc.) or a group which can be converted into the group which can form an anion, under the biological, that is, physiological conditions (e.g., a reaction in a living body such as oxidation, reduction and hydrolysis by an enzyme in living body) or chemically, or it may be a carboxyl group, or a prodrug thereof.

As the $R^2$, a group represented by the formula —CO-D [wherein D denotes (1) a hydroxyl group or (2) lower ($C_{1-4}$) alkoxy in which the alkyl part may be substituted with hydroxyl group, amino, halogen, lower ($C_{2-6}$)alkanoyloxy (e.g., acetoxy, pivaloyloxy etc.), lower ($C_{3-8}$)cycloalkanoyloxy, lower ($C_{1-6}$)alkoxycarbonyloxy (e.g., methoxycarbonyloxy, ethoxycarbonyloxy etc.), lower ($C_{3-8}$)cycloalkoxycarbonyloxy (e.g., cyclohexyloxycarbonyloxy etc.), lower ($C_{1-4}$)alkoxy or lower ($C_{3-8}$)cycloalkoxy] is preferable and, inter alia, carboxyl esterified with lower($C_{1-4}$)alkyl (preferably methyl or ethyl) is preferable.

In the above formula, examples of the "hydrocarbon residue" in the "hydrocarbon residue which may be bound via a hetero atom and may have a substituent" represented by $R^3$ include (1) an alkyl group, (2) an alkenyl group, (3) an alkynyl group, (4) a cycloalkyl group, (5) an aryl group, (6) an aralkyl group and the like, and, inter alia, an alkyl group, an alkenyl group and a cycloalkyl group are preferable.

The (1) alkyl group may be a straight or branched lower alkyl group having a carbon number of around 1 to 8, and examples thereof include methyl, ethyl, propyl, isopropyl, butyl, isobutyl, sec-butyl, t-butyl, pentyl, i-pentyl, hexyl, heptyl, octyl etc.

The (2) alkenyl group may be a straight or branched lower alkenyl group having a carbon number of around 2 to 8, and examples thereof include vinyl, propenyl, 2-butenyl, 3-butenyl, isobutenyl and 2-octenyl.

The (3) alkynyl group may be a straight or branched lower alkynyl group having a carbon number of around 2 to 8, and examples thereof include ethynyl, 2-propynyl, 2-butynyl, 2-penthynyl and 2-octynyl.

Examples of the (4) cycloalkyl group include lower cycloalkyl having a carbon number of around 3 to 6, for example, cyclopropyl, cyclobutyl, cyclopentyl and cyclohexyl.

The aforementioned alkyl group, alkenyl group, alkynyl group or cycloalkyl group may be substituted with a hydroxyl group, an optionally substituted amino group (e.g., amino, N-lower ($C_{1-4}$) alkylamino, N,N-di-lower ($C_{1-4}$)alkylamino etc.), halogen, lower ($C_{1-4}$)alkoxy group, or lower ($C_{1-4}$)alkylthio group.

Examples of the (5) aralkyl group include phenyl-lower ($C_{1-4}$)alkyl such as benzyl and phenethyl, and examples of the (6) aryl group include phenyl.

The aforementioned aralkyl group or aryl group may have, for example, halogen (e.g., F, Cl, Br etc.), nitro, optionally substituted amino group (e.g., amino, N-lower ($C_{1-4}$)alkylamino, N,N-di-lower ($C_{1-4}$)alkylamino etc.), lower ($C_{1-4}$) alkoxy (e.g., methoxy, ethoxy etc.), lower ($C_{1-4}$)alkylthio (e.g., methylthio, ethylthio etc.), or lower ($C_{1-4}$)alkyl (e.g., methyl, ethyl etc.) at an arbitrary position on the benzene ring.

Among the forgoing, as the "hydrocarbon residue" in the "hydrocarbon residue which may be bound via a hetero atom and may have a substituent" represented by $R^3$, an optionally substituted alkyl or alkenyl (e.g., lower ($C_{1-5}$)alkyl or lower ($C_{2-5}$)alkenyl group optionally substituted with hydroxyl group, amino group, halogen or lower ($C_{1-4}$)alkoxy group) is preferable and, inter alia, lower ($C_{1-5}$)alkyl (more preferably ethyl) is preferable.

Examples of the "hetero atom" in the "hydrocarbon residue which may be bound via a hetero atom and may have a substituent" represented by $R^3$ include —O—, —S(O)$_m$— [m denotes an integer of 0 to 2], —NR'— [R' denotes a hydrogen atom or lower ($C_{1-4}$)alkyl] and the like, and, inter alia, —O— is preferably used.

Among the foregoing, as $R^3$, a lower ($C_{1-5}$)alkyl group and lower ($C_{2-5}$)alkenyl group which may be bound via —O—, —S(O)$_m$— [m denotes an integer of 0 to 2] or —NR'—[R' denotes hydrogen atom or lower ($C_{1-4}$)alkyl] and may be substituted with an substituent selected from a hydroxyl group, an amino group, a halogen and a lower ($C_{1-4}$)alkoxy group are preferable, and, inter alia, lower ($C_{1-5}$)alkyl and lower ($C_{1-5}$)alkoxy (more preferable ethoxy) are preferable.

Among compounds having an angiotensin II antagonistic activity represented by the formula (I), a benzimidazole-7-carboxylic acid derivative represented by the formula (I'):

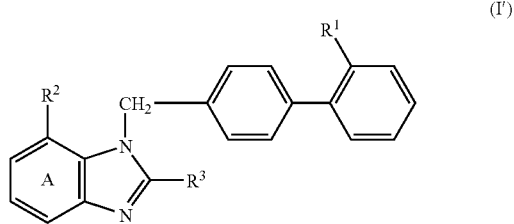

(wherein $R^1$ denotes (1) a carboxyl group, (2) a tetrazolyl group or (3) a group represented by the formula:

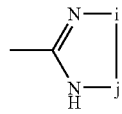

[wherein i denotes —O— or —S—, j denotes >=O, >=S or >=S(O)$_m$, and m is as defined above], ring A denotes a benzene ring optionally substituted with optionally substituted lower ($C_{1-4}$) alkyl (e.g., lower ($C_{1-4}$)alkyl optionally substituted with hydroxyl group, carboxyl group or halogen) or halogen in addition to the substituent $R^2$, preferably a benzene ring having no substituent other than the substituent $R^2$, $R^2$ denotes a group represented by the formula —CO-D [wherein D denotes (1) hydroxyl group or (2) lower ($C_{1-4}$) alkoxy in which the alkyl part may be substituted with hydroxyl group, amino, halogen, lower ($C_{2-6}$)alkanoyloxy (e.g., acetoxy, pivaloyloxy etc.), lower ($C_{3-8}$) cycloalkanoyloxy, lower ($C_{1-6}$)alkoxycarbonyloxy (e.g., methoxycarbonyloxy, ethoxycarbonyloxy etc.), lower ($C_{3-8}$) cycloalkoxycarbonyloxy (e.g., cyclohexyloxycarbonyloxy etc.), lower ($C_{1-4}$)alkoxy or lower ($C_{3-8}$)cycloalkoxy], $R^3$ denotes lower ($C_{1-5}$)alkyl or lower ($C_{2-5}$)alkenyl group which may be bound via —O—, —S(O)$_m$— [m denotes an integer of 0 to 2] or —NR'— [R' denotes hydrogen atom or lower ($C_{1-4}$)alkyl] and may be substituted with a substituent selected from a hydroxyl group, an amino group, a halogen and lower ($C_{1-4}$) alkoxy group (preferably lower ($C_{1-5}$)alkyl or lower ($C_{1-5}$) alkoxy; more preferably ethoxy)]), or a pharmaceutically acceptable salt thereof is preferable, and, inter alia, 2-ethoxy-1-[[2'-(1H-tetrazol-5-yl)biphenyl-4-yl]methyl]benzimidazole-7-carboxylic acid [Candesartan], 1-(cyclohexyloxycarbonyloxy)ethyl 2-ethoxy-1-[[2'-(1H-tetrazol-5-yl)biphenyl-4-yl]methyl]benzimidazole-7-carboxylate [Candesartan cilexetil], pivaloyloxymethyl 2-ethoxy-1-[[2'-(1H-tetrazol-5-yl)biphenyl-4-yl]methyl]benzimidazole-7-carboxylate, and 2-ethoxy-1-[[2'-(2,5-dihydro-5-oxo-1,2,4-oxadiazol-3-yl)biphenyl-4-yl]methyl]benzimidazole-7-carboxylic acid or a salt thereof etc. are preferable.

Of the aforementioned compounds having an angiotensin II antagonistic activity, 2-ethoxy-1-[[2'-(2,5-dihydro-5-oxo-1,2,4-oxadiazol-3-yl)biphenyl-4-yl]methyl]benzimidazole-7-carboxylic acid (hereinafter sometimes to be abbreviated as compound A) and a salt thereof are particularly preferable.

The aforementioned benzimidazole derivative can be synthesized by the known method described in, for example, EP-425921, EP-459136, EP-553879, EP-578125, EP-520423 and EP-668272 or a similar method. When Candesartan cilexetil is used, it is better to use the stable C-type crystal described in EP-459136.

A compound having an angiotensin II antagonistic activity or a prodrug thereof used in the present invention may be itself or a pharmaceutically acceptable salt thereof. When the compound having an angiotensin II antagonistic activity has an acidic group such as a carboxyl group and the like, examples of such the salt include salts with inorganic bases (e.g., alkali metal such as sodium, potassium etc., alkaline earth metal such as calcium, magnesium etc., transition metal such as zinc, iron, copper etc.) or salts with organic bases (e.g., organic amines such as trimethylamine, triethylamine, pyridine, picoline, ethanolamine, diethanolamine, triethanolamine, dicyclohexylamine and N,N'-dibenzylethylenediamine, basic amino acids such as arginine, lysine and ornithine).

When a compound having an angiotensin II antagonistic activity has a basic group such as an amino group and the like, examples are salts with inorganic acids or organic acids (e.g., hydrochloric acid, nitric acid, sulfuric acid, phosphoric acid, carbonic acid, bicarbonic acid, formic acid, acetic acid, propionic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid etc.) or acidic amino acids such as aspartic acid and glutamic acid.

A prodrug of a compound having an angiotensin II antagonistic activity used in the present invention [hereinafter, referred to as AII antagonistic compound in some cases] refers to a compound which is converted into the AII antagonistic compound by a reaction with an enzyme, stomach acid or the like under the physiological conditions in a living body, that is, a compound which undergoes enzymatic oxidation, reduction, hydrolysis or the like, and is changed into the AII antagonistic compound, or a compound which undergoes hydrolysis by stomach acid or the like, and is changed into the AII antagonistic compound. Examples of a prodrug of the AII antagonistic compound include a compound in which an amino group of the AII antagonistic compound is acylated, alkylated or phosphorylated (e.g., a compound in which an amino group of the AII antagonistic compound is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated or tert-butylated); a compound in which a hydroxyl group of the AII antagonistic compound is acylated, alkylated, phosphorylated or borated (e.g., a compound in which a hydroxyl group of the AII antagonistic compound is acetylated, palmitoylated, propanoylated, pivaloylated, succinylated, fumarylated, alanylated or dimethylaminomethylcarbonylated); a compound in which a carboxyl group of the AII antagonistic compound is esterified or amidated (e.g., a compound in which a carboxyl group of the AII antagonistic compound is ethylesterified, phenylesterified, carboxymethylesterified, dimethylaminomethylesterified, pivaloyloxymethylesterified, ethoxycarbonyloxyethylesterified, phthalidylesterified, (5-methyl-2-oxo-1,3-dioxolen-4-yl)methylesterified, cyclohexyloxycarbonyloxyethylesterified, or methylamidated); and the like. These compounds can be prepared from the AII antagonistic compound by the known method per se. Alternatively, a prodrug of the AII antagonistic compound may be a prodrug which is changed into the AII antagonistic compound under the physiological conditions described in "Development of Medicaments", vol. 7, Molecular Design, pp 163-198 published by Hirokawashoten in 1990.

The AII antagonistic compound may be either a hydrate or a non-hydrate.

The PPARγ agonist-like substance used in the present invention only needs to be an agonist against PPARγ, and may be any substance as long as it expresses the activity.

The PPARγ agonist-like substance is preferably, for example, a substance showing a clear PPARγ agonist-like activity in vitro at a concentration of not more than 10 μM and the like.

As preferable examples of the PPARγ agonist-like substance, insulin sensitizers such as troglitazone, rosiglitazone, englitazone, ciglitazone, pioglitazone, $PGJ_2$, GI-262570, JTT-501, MCC-555, YM-440, KRP-297, CS-011, FK-614 and the like can be mentioned.

In the present invention, the compound having an angiotensin II antagonistic activity and a PPARγ agonist-like substance is not limited to the above-mentioned examples and any substance can be used as long as it has such activity. In addition, the substance may further have a PPARα functional regulatory activity (agonistic or antagonistic activity).

The agent of the present invention may contain a compound having an angiotensin II antagonistic activity in combination with a PPARγ agonist-like substance, and as preferable combinations, for example, a combination of the aforementioned insulin sensitizer having a PPARγ agonistic activity (e.g., troglitazone, rosiglitazone, englitazone, ciglitazone, pioglitazone and the like) and compound A and the like can be mentioned.

As the insulin sensitizer having a PPARγ agonistic activity, for example, troglitazone has been reported to show a body weight gaining action in patients with type II diabetes (Diabetes, 47, suppl. 1, A18, No. 69, 1998). The body weight gain in patients with diabetes induces edema and swelling, and aggravation of symptoms may cause a grave circulatory diseases such as cardiac hypertrophy and the like, causing a serious problem in the treatment of diabetes.

Therefore, the use of a compound per se, which has an angiotensin II antagonistic activity and an insulin resistance-improving activity in combination, such as compound A, can avoid use of an insulin sensitizer causing body weight gain, or can markedly decrease the dose of an insulin sensitizer itself. As compared to the single use of an insulin sensitizer, a combined use with an insulin sensitizer strikingly suppresses an expression of body weight gain or a possibility thereof, which in turn highly advantageously avoids aggravation of diabetic symptoms.

The dose of the agent of the present invention only needs to fall within the range of an effective amount of each substance.

For example, while the dose of a compound having an angiotensin II antagonistic activity varies depending on the subject of administration, administration route, target disease, symptom and the like, in the case of oral administration to an adult patient with diabetes (body weight 60 kg), a dose is generally about 0.001 to about 500 mg, preferably about 0.1 to about 100 mg, more preferably about 2.5 to about 60 mg, which is administered in 1 to 3 portions a day.

The dose of a PPARγ agonist-like substance to patients with diabetes is about 0.1 to about 600 mg/day, preferably about 0.5 to about 240 mg/day, more preferably about 1.0 to about 100 mg/day. These amounts may be administered once a day or in 2 or 3 portions a day.

The administration ratio of a compound having an angiotensin II antagonistic activity and a PPARγ agonist-like substance (PPARγ agonist-like substance/compound having an angiotensin II antagonistic activity) is about 0.002 to about 60000, preferably about 0.005 to about 2400, more preferably about 0.02 to about 40, more preferably about 0.4 to about 8.

The body weight gain inhibitor of the present invention (hereinafter sometimes to be simply abbreviated as an "agent of the present invention") shows low toxicity, and can be used as it is or as a pharmaceutical composition by mixing with a pharmacologically acceptable carrier by a method known per se, as a prophylactic/therapeutic agent for after-mentioned various diseases in mammals (e.g., human, mouse, rat, rabbit, dog, cat, bovine, horse, swine, monkey and the like).

Herein, as a pharmaceutically acceptable carrier, various organic or inorganic carrier materials which are conventional as a pharmaceutical material are used, and is incorporated as an excipient, a lubricant, a binder or a disintegrating agent in a solid preparation; as a solvent, a solubilizer, a suspending agent, an isotonic, a buffer or a soothing agent in a liquid preparation. If necessary, pharmaceutical additives such as a preservative, an antioxidant, a colorant and a sweetener may be used.

Preferable examples of the excipient include lactose, sucrose, D-mannitol, D-sorbitol, starch, gelatinized starch, dextrin, crystalline cellulose, low-substituted hydroxypropylcellulose, sodium carboxymethylcellulose, gum arabic, dextrin, pullulan, light silicic anhydride, synthetic aluminum silicate and magnesium aluminate metasilicate.

Preferable examples of the lubricant include magnesium stearate, calcium stearate, talc and colloidal silica.

Preferable examples of the binder include gelatinized starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrating agent include lactose, sucrose, starch, carboxymethylcellulose, calcium carboxylmethylcellulose, sodium crosscarmerose, sodium carboxymethylstarch, light silicic anhydride and low-substituted hydroxypropylcellulose.

Preferable examples of the solvent include water for injection, physiological saline, Ringer's solution, alcohol, propylene glycol, polyethylene glycol, sesame oil, corn oil, olive oil and cottonseed oil.

Preferable examples of the solubilizer include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium laurylsulfate, laurylaminopropionic acid, lecithin, benzalkonium chloride, benzethonium chloride and monostearic acid glycerin; hydrophilic polymers such as polyvinyl alcohol, polyvinyl pyrrolidone, sodium carboxymethylcellulose, methylcellulose, hydroxymethylcellulose, hydroxyethylcellulose and hydroxypropylcellulose; polysorbates and polyoxyethylene hydrogenated castor oil.

Preferable examples of the isotonic include sodium chloride, glycerin, D-mannitol, D-sorbitol and glucose.

Preferable examples of a buffer include buffers such as phosphate, acetate, carbonate and citrate.

Preferable examples of the soothing agent include benzyl alcohol.

Preferable examples of the preservative include paraoxy benzoic acid esters, chlorobutanol, benzyl alcohol, phenethyl alcohol, dehydroacetic acid and sorbic acid.

Preferable examples of the antioxidant include sulfite and ascorbate.

Preferable examples of the colorant include water-soluble edible tar pigments (e.g., edible pigments such as edible red Nos. 2 and 3, edible yellow Nos. 4 and 5, edible blue Nos. 1 and 2), water-insoluble lake pigments (e.g., aluminum salt of the aforementioned water-soluble tar pigments), and natural pigments (e.g., β-carotene, chlorophyll and colcothar).

Preferable examples of the sweetener include sodium saccharine, dipotassium glycyrrhizinate, aspartame and stevia.

The dosage form of the pharmaceutical composition includes oral preparations such as tablets, capsules (including soft capsules and microcapsules), granules, powders, syrups, emulsions, suspensions and sustained-releasing preparations; and parenteral preparations such as injections (e.g., subcutaneous injection, intravenous injection, intramuscular injection, intraperitoneal injection, intravitreous injection), eye drops, external preparations (e.g., transnasal preparation, transdermal preparation and ointment), suppositories (e.g., rectal suppository and vaginal suppository), pellets and drops, and these can be safely administered either orally or parenterally.

The pharmaceutical compositions can be prepared by conventional methods in the technical field of pharmacy, such as the methods described in the Japanese Pharmacopoeia. Specific process for producing preparations will be described in detail below.

For example, oral preparations are produced by adding, for example, an excipient (e.g., lactose, sucrose, starch, D-mannitol etc.), a disintegrating agent (e.g., calcium carboxymethylcellulose etc.), a binder (e.g., gelatinized starch, gum arabic, carboxymethylcellulose, hydroxypropylcellulose, polyvinylpyrrolidone etc.) or a lubricant (e.g., talc, magnesium stearate, polyethylene glycol 6000 etc.) to an active ingredient, compression-molding them and, if necessary, coating the molded material with a coating base by a method known per se for the purpose of taste masking, enteric coating or sustainability.

Examples of the coating base include a sugar-coated base, a water-soluble film coating base, an enteric film coating base, a sustained-releasing film coating base and the like.

As the sugar-coated base, sucrose is used, and one or two or more members selected from talc, precipitated calcium carbonate, gelatin, gum arabic, pullulan, carnauba wax and the like may be used jointly.

Examples of the water-soluble film coating base include cellulose polymers such as hydroxypropylcellulose, hydroxypropylmethylcellulose, hydroxyethylcellulose and methylhydroxyethylcellulose; synthetic polymers such as polyvinylacetal diethylaminoacetate, aminoalkyl methacrylate copolymer E [Eudragit E (trade name), Rohmpharma] and polyvinylpyrrolidone; polysaccharides such as pullulan.

Examples of the enteric film coating base include cellulose polymers such as hydroxypropylmethylcellulose phthalate, hydroxypropylmethylcellulose acetate succinate, carboxymethylethylcellulose, and cellulose acetate phthalate; acrylic acid polymers such as methacrylic acid copolymer L [Eudragit L (trade name), Rohmpharma], methacrylic acid copolymer LD [Eudragit L-30D55 (trade mane), Rohmpharma], and methacrylic acid copolymer S [Eudragit S (trade name), Rohmpharma]; and natural materials such as shellac.

Examples of the sustained-release film coating base include cellulose polymers such as ethylcellulose; acrylic acid polymers such as aminoalkyl methacrylate copolymer RS [Eudragit RS (trade name) Rohmpharma], and ethyl acrylate/methyl methacrylate copolymer suspension [Eudragit NE (trade name), Rohmpharma].

The aforementioned coating bases may be used by mixing two or more kinds of them at an appropriately ratio. In addition, upon coating, a light shielding agent such as titanium oxide and iron sesquioxide may be used.

Injections are prepared by dissolving, suspending or emulsifying an active ingredient together with a dispersing agent (e.g., polysorbate 80, polyoxyethylene hydrogenated castor oil 60, polyethylene glycol, carboxymethylcellulose, sodium arginate etc.), a preservative (e.g., methylparaben, propylparaben, benzyl alcohol, chlorobutanol, phenol etc.), an isotonic (e.g., sodium chloride, glycerin, D-mannitol, D-sorbitol, glucose etc.) in an aqueous solvent (e.g., distilled water, physiological saline, Ringer's solution etc.) or an oily solvent (e.g., vegetable oil such as olive oil, sesame oil, cottonseed, corn oil etc. propylene glycol). Upon this, additives such as a solubilizer (e.g., sodium salicylate, sodium acetate etc.), a stabilizer (e.g., human albumin etc.) and a soothing agent (benzyl alcohol etc.) may be used.

The content of a compound having an angiotensin II antagonistic activity in a pharmaceutical composition is generally about 0.01 to about 99.9% by weight, preferably about 0.1 to about 50% by weight, of the whole preparation.

As mentioned above, since a compound having an angiotensin II antagonistic activity represented by compound A shows a body weight gain suppressing action, it can be used as a body weight gain inhibitor for a mammal. The mammal to be the applicable target only needs to an animal wishing to avoid body weight gain and may be an animal genetically having a risk of body weight gain or an animal suffering from a life-style related disease such as diabetes, hypertension and/or hyperlipidemia and the like. The body weight gain may be caused by excessive food ingestion or dietary habit without nutritional balance, or induced by a prophylactic/therapeutic agent for the aforementioned life-style related diseases. In addition, the body weight gain may be that before reaching obesity, or that of a patient with obesity. As used herein, the obesity is defined by a BMI (Body Mass Index: body weight (kg)÷[body height (m)]$^2$) of not less than 25 (based on the criteria of JAPAN SOCIETY FOR THE STUDY OF OBESITY) for Japanese, and a BMI of not less than 30 (based on WHO criteria) for Westerners.

While the agent of the present invention is preferably used as a body weight gain inhibitor for obese patients with diabetes, it can be also used for the purpose of suppressing a body weight gain of obese patients suffering from various complications such as insulin resistance, impaired glucose tolerance; diabetes such as insulin non-dependent diabetes, type II diabetes, type II diabetes associated with insulin resistance, type II diabetes associated with impaired glucose tolerance etc.; various complications such as hyperinsulinemia, hypertension associated with insulin resistance, hypertension associated with impaired glucose tolerance, hypertension associated with diabetes (e.g., type II diabetes etc.), hypertension associated with hyperinsulinemia, insulin resistance occurring in association with hypertension, impaired glucose tolerance occurring in association with hypertension, diabetes occurring in association with hypertension, hyperinsulinemia occurring in association with hypertension, diabetic complications [e.g., microangiopathy, diabetic neuropathy, diabetic nephropathy, diabetic retinopathy, diabetic cataract, large vessel disease, osteopenia, diabetic hyperosmolar coma, infectious diseases (e.g., respiratory infectious disease, urinary tract infectious disease, digestive infectious disease, infectious disease of dermal soft tissue, infectious disease of inferior limb etc.), diabetic gangrene, dry mouth, lowered sense of hearing, diabetic cerebrovascular disorder, diabetic peripheric hematogenous disorder, diabetic hypertension and the like], diabetic cachexia, diabetic nephropathy and the like.

As applicable diseases for the compound having an angiotensin II antagonistic activity as a physiologically active compound, diseases developed or whose onset is promoted by contraction and growth of blood vessels or organ disorders that express via angiotensin II receptor, by the presence of angiotensin II, or by the factors induced by the presence of angiotensin II and the like can be mentioned.

As such diseases, for example, hypertension, blood pressure circadian rhythm abnormality, heart diseases (e.g., cardiac hypertrophy, acute heart failure and chronic heart failure including congestive heart failure, cardiac myopathy, angina pectoris, myocarditis, arrhythmia, tachycardia, cardiac infraction etc.), cerebrovascular disorders (e.g., asymptomatic cerebrovascular disorder, transient ischemic attack, cerebral stroke, cerebrovascular dementia, hypertensive encephalopathy, cerebral infarction etc.), cerebral edema, cerebral circulatory disorder, recurrence and sequela of cerebrovascular disorders (e.g., neurotic symptom, psychic symptom, subjective symptom, disorder in daily living activities etc.), ischemic peripheral circulation disorder, myocardial ischemia, venous insufficiency, progression of cardiac insufficiency after cardiac infarction, renal diseases (e.g., nephritis, glomerulonephritis, glomerulosclerosis, renal failure, thrombotic microvasculopathy, complication of dialysis, organ dysfunction including nephropathy by radiation damage etc.), arteriosclerosis including atherosclerosis (e.g., aneurysm, coronary arteriosclerosis, cerebral arteriosclerosis, peripheral arteriosclerosis etc.), vascular hypertrophy, vascular hypertrophy or obliteration and organ disorders after intervention (e.g., percutaneous transluminal coronary angioplasty, stenting, coronary angioscopy, intravascular ultrasound, intracoronary thrombolytic therapy etc.), vascular re-obliteration and restenosis after bypass, polycythemia, hypertension, organ disorder and vascular hypertrophy after transplantation, rejection after transplantation, ocular diseases (e.g., glaucoma, ocular hypertension etc.), thrombosis, multiple organ disorder, endothelial dysfunction, hypertensive tinnitus, other cardiovascular diseases (e.g., deep vein thrombosis, obstructive peripheral circulatory disorder, arteriosclerosis obliterans, obstructive thromboangiitis, ischemic cerebral circulatory disorder, Raynaud's disease, Berger disease etc.), metabolic and/or nutritional disorders (e.g., obesity, hyperlipidemia, hypercholesterolemia, hyperuricacidemia, hyperkalemia, hypernatremia etc.), nerve degeneration diseases (e.g., Alzheimer's disease, Parkinson's syndrome, amyotrophic lateral sclerosis, AIDS encephalopathy etc.), central nervous system disorders (e.g., cerebral hemorrhage, cerebral infarction, their sequela and complication, head injury, spinal injury, cerebral edema, sensory malfunction, sensory functional disorder, autonomic nervous system disorder, autonomic nervous system malfunction, multiple sclerosis etc.), dementia, defects of memory, disorder of consciousness, amnesia, anxiety symptom, catatonic symptom, discomfort mental state, psychopathies (e.g., depression, epilepsy, alcoholism etc.), inflammatory diseases (e.g., arthritis such as rheumatoid arthritis, osteoarthritis, rheumatoid myelitis, periostitis etc.; inflammation after operation and injury; remission of swelling; pharyngitis; cystitis; pneumonia; atopic dermatitis; inflammatory intestinal diseases such as Crohn's disease, ulcerative colitis etc.; meningitis; inflammatory ocular disease; inflammatory pulmonary disease such as pneumonia, pulmonary silicosis, pulmonary sarcoidosis, pulmonary tuberculosis etc.), allergic diseases (e.g., allergic rhinitis, conjunctivitis, gastrointestinal allergy, pollinosis, anaphylaxis etc.), chronic obstructive pulmonary disease, interstitial pneumonia, pneumocytis carinni pneumonia, collagen diseases (e.g., systemic lupus erythematodes, scleroderma, polyarteritis etc.), hepatic diseases (e.g., hepatitis including chronic hepatitis, hepatic cirrhosis etc.), portal hypertension, digestive system disorders (e.g., gastritis, gastric ulcer, gastric cancer, gastric disorder after operation, dyspepsia, esophageal ulcer, pancreatitis, colon polyp, cholelithiasis, hemorrhoidal disease, varices ruptures of esophagus and stomach etc.), blood and/or myelopoietic diseases (e.g., erythrocytosis, vascular purpura, autoimmune hemolytic anemia, disseminated intravascular coagulation syndrome, multiple myelopathy etc.), bone diseases (e.g., fracture, refracture, osteoporosis, osteomalacia, bone Paget's disease, sclerosing myelitis, rheumatoid arthritis, osteoarthritis of the knee and joint tissue dysfunction owing to similar diseases and disorder etc.), solid tumor, tumors (e.g., malignant melanoma, malignant lymphoma, cancer of digestive organs (e.g., stomach, intestine etc.) etc.), cancer and cachexia following cancer, metastasis cancer, endocrinopathy (e.g., Addison's disease, Cushing's syndrome, pheochromocytoma, primary aldosteronism etc.), Creutzfeldt-Jakob disease, urinary organ and/or male genital diseases (e.g., cystitis, prostatic hypertrophy, prostatic cancer, sex infectious disease etc.), female disorders (e.g., climacteric disorder, gestosis, endometriosis, hysteromyoma, ovarian disease, breast disease, sex infectious disease etc.), disease relating to environment and occupational factors (e.g., radiation hazard, hazard by ultraviolet, infrared, or laser beam, altitude sickness etc.), respiratory diseases (e.g., cold syndrome, pneumonia, asthma, pulmonary hypertension, pulmonary thrombosis and pulmonary embolism etc.), infectious diseases (e.g., viral infectious diseases with cytomegalovirus, influenza virus, herpes virus etc., rickettsiosis, bacterial infectious disease etc.), toxemias (e.g., sepsis, septic shock, endotoxin shock, Gram-negative sepsis, toxic shock syndrome etc.), otorhinolaryngological diseases (e.g., Meniere's syndrome, tinnitus, dysgeusia, vertigo, disequilibrium, dysphagia etc.), skin diseases (e.g., keloid, hemangioma, psoriasis etc.), intradialytic hypotension, myasthenia gravis, systemic diseases such as chronic fatigue syndrome and the like can be mentioned.

In addition, long-term suppression of action of angiotensin II results in the improvement or suppression of promotion of disorder or abnormality in the biofunction and physiological action, that causes adult disorders and various diseases linked with aging and the like, which in turn leads to the primary and secondary prophylaxis of diseases or clinical conditions caused thereby or suppression of the progression thereof. As the disorder or abnormality in the biofunction and physiological action, for example, disorder or abnormality in automatic controlling capability of cerebral circulation and/or renal circulation, disorder of circulation (e.g., peripheral, cerebral, microcirculation etc.), disorder of blood-brain-barrier, salt susceptibility, abnormal state of coagulation and fibrinolysis system, abnormal state of blood and blood cell components (e.g., accentuation of platelet aggregation action, malfunction of erythrocyte deformability, accentuation of leukocyte adhesiveness, rise of blood viscosity etc.), production and function accentuation of growth factor and cytokines (e.g., PDGF, VEGF, FGF, interleukin, TNF-α, MCP-1 etc.), accentuation of production and infiltration of inflammatory cells, accentuation of production of free radical, liposteatosis accentuation, endothelial function disorder, endothelium, cell and organ dysfunction, edema, cell morphogenesis change of smooth muscle etc. (morphogenesis to proliferation type etc.), production and function accentuation of vasoactive substance and thrombosis inducers (endothelin, thromboxane $A_2$ etc.), abnormal constriction of blood vessel etc., metabolic disorder (serum lipid abnormalities, dysglycemia etc.), abnormal growth of cell etc., angiogenesis (including abnormal vasculogenesis during abnormal capillary reticular formation in adventitial coat of arteriosclerotic lesion) and the like can be mentioned. Of these, the present invention can be used as an agent for the primary and secondary prophylaxis or treatment of organ disorders associated with various diseases (e.g., cerebrovascular disorder and organ disorder associated therewith, organ disorder associated with circulatory disease, organ disorder associated with diabetes, organ disorder after intervention etc.) can be mentioned. Therefore, the agent of the present invention can be advantageously used for patients who should suppress body weight gain, and who have concurrently developed the above-mentioned diseases.

When a compound having an angiotensin II antagonistic activity is used in combination with a PPARγ agonist-like substance in the present invention, these may be administered as independent preparations or may be administered as a single combined preparation. When used in a combination of independent preparations, the timing of administration of each preparation is not limited, and these may be simultaneously administered to a subject of administration, or may be administered in a staggered manner. The dosage forms of respective preparations may be different, and the dosage form may be determined for each active ingredient, which is employed for conventional pharmaceutical agents.

When a PPARγ agonist-like substance to be used concurrently is made into a preparation independent from the compound having an angiotensin II antagonistic activity, the agent containing the PPARγ agonist-like substance may contain pharmacologically acceptable carriers. As such carriers, various organic or inorganic carrier substances conventionally used as materials for preparations can be used, and added as excipient, lubricant, binder and disintegrant for solid preparations; solvent, dissolution aids, suspending agent, isotonizing agent, buffer and soothing agent for liquid preparations; and the like. Where necessary, additives for preparation, such as preservative, antioxidant, coloring agent, sweetening agent and the like, can be also used.

As the carrier or additive, those similar to the aforementioned can be mentioned.

The content of a PPARγ agonist-like substance in a pharmaceutical composition containing the PPARγ agonist-like substance is generally about 0.01 to about 99.9% by weight, preferably about 0.1 to about 50% by weight, of the whole preparation.

The agent of the present invention is effective for the suppression of body weight gain observed in patient with various diseases (e.g., diabetes and the like) and under medication of a PPARγ agonist-like substance (e.g., insulin sensitizer) and useful for the treatment/prophylaxis and the like of the angiotensin II-related diseases (e.g., the above-mentioned hypertension and the like).

The agent of the present invention can suppress a body weight gain induced by a PPARγ agonist-like substance, which is observed in patients (e.g., patients with diabetes) under medication of a PPARγ agonist-like substance to, for example, not more than about 80%.

The applicable diseases of the PPARγ agonist-like substance include, for example, diabetes (e.g., type I diabetes, type II diabetes, gestational diabetes mellitus and the like), hyperlipidemia (e.g., hypetriglyceridemia, hypercholesterolemia, hypo-high density lipoproteinemia, postprandial hyperlipidemia and the like), diabetic complications (e.g., neuropathy, nephropathy, retinopathy, cataract, macroangiopathy, osteopenia and the like), impaired glucose tolerance (IGT), obesity, osteoporosis, cachexia (e.g., carcinomatous cachexia, tuberculous cachexia, diabetic cachexia, cachexia due to hemopathy, cachexia due to endocrinopathy, cachexia due to infection, or cachexia due to acquired immune deficiency syndrome), fatty liver, hypertension, polycystic ovary syndrome, gestational diabetes mellitus, renal diseases (e.g., diabetic nephropathy, glomerulonephritis, glomerulosclerosis, nephrotic syndrome, hypertensive nephrosclerosis, end stage renal disease and the like), muscular dystrophy, myocardial infarction, angina pectoris, cerebrovascular disorders (e.g., cerebral infarction, stroke), insulin resistance syndrome, Syndrome X, hyperinsulinemia, sensory disturbance in hyperinsulinemia, tumors (e.g., leukemia, breast cancer, prostatic cancer, skin carcinoma and the like), irritable bowel syndrome, acute or chronic diarrhea, visceral obesity syndrome and the like. In addition, the PPARγ agonist-like substance can be used for the treatments aiming at improved insulin resistance, enhanced insulin sensitivity, and suppression of the shift from impaired glucose tolerance to diabetes. Furthermore, the agent of the present invention can be used for controlling appetite and food ingestion in the patients undergoing treatments of diabetes.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, regarding diagnostic criteria for diabetes, new diagnostic criteria were reported by ADA (The American Diabetes Association) in 1997 and by WHO in 1998.

According to these reports, diabetes is a condition where the fasting blood glucose level (glucose concentration in venous plasma) is not less than 126 mg/dl, and the 2-hour value (glucose concentration in venous plasma) of the 75 g oral glucose tolerance test is not less than 200 mg/dl.

In addition, according to the above reports, impaired glucose tolerance is a condition where the fasting blood glucose level (glucose concentration in venous plasma) is less than 126 mg/dl, and the 2-hour value (glucose concentration in venous plasma) of the 75 g oral glucose tolerance test is not less than 140 mg/dl and less than 200 mg/dl. Furthermore, according to the ADA report, a condition where the fasting blood glucose level (glucose concentration in venous plasma) is not less than 110 mg/dl and less than 126 mg/dl, is called IFG (Impaired Fasting Glucose). On the other hand, according to the WHO report, of the conditions of IFG (impaired fasting glucose), a condition where the 2-hour value (glucose concentration in venous plasma) of the 75 g oral glucose tolerance test is less than 140 mg/dl, is called IFG (impaired Fasting Glycemia).

PPARγ agonist-like substance can be used as an agent for the prophylaxis or treatment of diabetes, borderline type, impaired glucose tolerance, IFG (Impaired Fasting Glucose) and IFG (Impaired Fasting Glycemia) as defined by the above-mentioned new diagnostic criteria. Moreover, the agent of the present invention can prevent the progression of the borderline type, impaired glucose tolerance, IFG (Impaired Fasting Glucose) or IFG (Impaired Fasting Glycemia) to diabetes.

In addition, the agent of the present invention can be used in combination with pharmaceutical agents such as a therapeutic agent for diabetes, a therapeutic agent for diabetic complications, an anti-hyperlipidemia agent, an anti-hypertensive agent, a diuretic, a chemotherapeutic agent, an immunotherapeutic agent and the like (hereinafter to be abbreviated as a combination drug). In addition, the agent per se of the present invention may contain such combination drugs. Unless otherwise specified, when simply expressed by "in combination with" in the present specification, they may be administered as independent drugs or may be administered as a single combined drug. When used in a combination of independent drugs, the timing of administration of the agent of the present invention and a combination drug is not limited, and these may be simultaneously administered to a subject of administration, or may be administered in a staggered manner. Furthermore, two or more kinds of combination drugs may be used in combination at an appropriate ratio.

The dose of the combination drug can be suitably determined based on the dose clinically employed for each agent. In addition, the mixing ratio of the agent of the present invention and a combination drug can be determined depending on the subject to be administered, administration route, subject disease, the symptom, combination and the like.

As the therapeutic agent for diabetes include insulin preparations (e.g., animal insulin preparations extracted from the bovine or swine pancreas; human insulin preparations synthesized by a genetic engineering technique using *E. coli* or a yeast), α-glucosidase inhibitors (e.g., voglibose, acarbose, miglitol, emiglitate etc.), biguanide agents (e.g., phenformin, metformin, buformin etc.), insulin secretagogues [e.g., sulfonylurea agents (e.g., tolbutamide, glibenclamide, gliclazide, chlorpropamide, tolazamide, acetohexamide, glyclopyramide, glimepiride, glipizide, glybuzole etc.), repaglinide, senaglinide, nateglinide, mitiglinide or its calcium salt hydrate, GLP-1 etc.], amylin agonists (e.g., pramlintide etc.), phosphotyrosine phosphatase inhibitors (e.g., vanadic acid etc.) and the like can be mentioned.

As the therapeutic agents for diabetic complications, aldose reductase inhibitors (e.g., tolrestat, epalrestat, zenarestat, zopolrestat, minalrestat, fidarestat, SNK-860, CT-112 etc.), neurotrophic factors (e.g., NGF, NT-3, BDNF etc.), neurotrophic factor production-promoting agents, PKC inhibitors (e.g., LY-333531 etc.), AGE inhibitors (e.g., ALT946, pimagedine, pyratoxathine, N-phenacylthiazolium bromide (ALT766), EXO-226 etc.), active oxygen scavengers (e.g., thioctic acid etc.) and cerebral vasodilators (e.g., tiapride, mexiletine etc.) can be mentioned.

As the anti-hyperlipidemia agents, statin compounds which are cholesterol synthesis inhibitors (e.g., pravastatin, simvastatin, lovastatin, atorvastatin, fluvastatin, cerivastatin, itavastatin or salts thereof (e.g., sodium salt) etc.), squalene synthetase inhibitors or fibrate compounds having a triglyceride lowering effect (e.g., bezafibrate, clofibrate, simfibrate, clinofibrate etc.) and the like can be mentioned.

As the antihypertensive agents, angiotensin converting enzyme inhibitors (e.g., captopril, enalapril, delapril etc.), angiotensin II antagonists (e.g., losartan, candesartan cilexetil, eprosartan, valsartan, termisartan, irbesartan, tasosartan, olmesartan etc.), calcium antagonists (e.g., manidipine, nifedipine, amlodipine, efonidipine, nicardipine etc.) and the like can be mentioned.

As the anti-obesity agents, for example, central acting anti-obesity agent (e.g., dexfenfluramine, fenfluramine, phentermine, sibutramine, amfepramone, dexamphetamine, mazindol, phenylpropanolamine, clobenzorex etc.), pancreatic lipase inhibitors (e.g., orlistat etc.), β3 agonists (e.g., CL-316243, SR-58611-A, UL-TG-307, SB-226552, AJ-9677, BMS-196085, AZ40140 etc.), anorectic peptides (e.g., leptin, CNTF (ciliary neurotropic factor) etc.), cholecystokinin agonists (e.g., lintitript, FPL-15849 etc.) and the like can be mentioned.

As the diuretics, for example, xanthine derivatives (e.g., theobromine sodium salicylate, theobromine calcium salicylate etc.), thiazide preparations (e.g., ethiazide, cyclopenthiazide, trichlormethiazide, hydrochlorothiazide, hydroflumethiazide, benzylhydrochlorothiazide, penfluthiazide, polythiazide, methyclothiazide etc.), anti-aldosterone preparations (e.g., spironolactone, triamterene etc.), carbonic anhydrase inhibitors (e.g., acetazolamide etc.), chlorobenzenesulfonamide preparations (e.g., chlortalidone, mefruside, indapamide etc.), azosemide, isosorbide, ethacrynic acid, piretanide, bumetanide, furosemide and the like can be mentioned.

As the chemotherapeutic agents, for example, alkylation agents (e.g., cyclophosphamide, ifosphamide etc.), metabolic antagonists (e.g., methotrexate, 5-fluorouracil etc.), anticancer antibiotics (e.g., mitomycin, adriamycin etc.), plant-derived anticancer agents (e.g., vincristine, vindesine, taxol etc.), cisplatin, carboplatin, etoposide and the like can be mentioned. Of these, furtulon, neofurtulon and the like which are 5-fluorouracil derivatives are preferable.

As the immunotherapeutic agents, for example, icroorganism or bacterial components (e.g., muramyl dipeptide derivative, picibanil etc.), polysaccharides having immunostimulant action (e.g., lenthinan, schizophyllan, krestin etc.), cytokines obtained by genetic engineering techniques (e.g., interferon, interleukin (IL) etc.), colony stimulating factor (e.g., granulocyte-colony stimulating factor, erythropoietin etc.) and the like can be mentioned, with preference given to IL-1, IL-2, IL-12 and the like.

Moreover, pharmaceutical agents having a cachexia improving action acknowledged in animal models and clinical situations, which include cyclooxygenase inhibitors (e.g., indomethacin etc.)[*Cancer Research*, Vol. 49, pp. 5935-5939, 1989], progesterone derivatives (e.g., megestrol acetate) [*Journal of Clinical Oncology*, Vol. 12, pp. 213-225, 1994], glucosteroid (e.g., dexamethasone etc.), metoclopramide pharmaceutical agents, tetrahydrocannabinol pharmaceutical agent (publications are the same as the above), fat metabolism improving agents (e.g., eicosapentanoic acid etc.)[*British Journal of Cancer*, Vol. 68, pp. 314-318, 1993], growth hormone, IGF-1, and antibody against TNF-α, LIF, IL-6 or oncostatin M, which is a factor inducing cachexia, and the like, can be also used in combination with the pharmaceutical agent of the present invention.

The combination drug preferably includes:
1) an insulin preparation;
2) a biguanide agent;
3) an insulin secretagogue (such as sulfonylurea agent);
4) a biguanide agent;
5) an α-glucosidase inhibitor;
6) an insulin preparation and a biguanide agent;
7) an insulin preparation and α-glucosidase inhibitor;
8) an insulin secretagogue (such as sulfonylurea agent) and a biguanide agent;
9) an insulin secretagogue (such as sulfonylurea agent) and an α-glucosidase inhibitor;
10) a biguanide agent and an α-glucosidase inhibitor;
11) an insulin sensitizer (e.g., PPARγ agonist-like substance);
12) a combination of an insulin sensitizer and the agent of the above-mentioned 1) to 10);
13) reducer of blood sugar and other therapeutic agent for diabetic complication;
14) other agents mentioned above and a combination of two or more kinds thereof;

When the agent of the present invention is used in combination with a combination drug, the amounts of these agents can be decreased in a safe range in consideration of opposition effect of these agents. Particularly, the dose of insulin secretagogues such as insulin preparation, sulfonylurea agent and the like, and biguanide agents can be decreased from conventional dose. Therefore, the side effects that will be caused by these agents can be safely prevented. In addition, the doses of the agents for diabetic complications, antilipidemic agents and anti-hypertensive agents can be decreased. As a result, the side effects that will be caused by these agents can be effectively prevented.

The present invention is explained in more detail in the following by referring to Experimental Examples and Examples, which are not to be construed as limitative.

In the prescription shown as Examples, the components (additives) other than the active ingredient can be those listed in the Japanese Pharmacopoeia, Japanese Pharmaceutical Codex or Japanese Pharmaceutical Excipients and the like.

EXPERIMENTAL EXAMPLE 1

Effect of 2-ethoxy-1-[[2'-(2,5-dihydro-5-oxo-1,2,4-oxadiazole-3-yl)biphenyl-4-yl]methyl]benzimidazole-7-carboxylic acid (Compound A) on Body Weight Gain of Obese Mouse
1) Test Method As the obese mouse, male KKA$^y$ mice (10 week old) were used. The mice were grouped by measuring the body weight, and feeding of a CE-2 powdered feed (control)(n=7) and a 0.005% compound A-mixed feed (n=7) was started. At 4 days from feeding, the body weight was measured and the amount of the body weight gain was calculated. As the normal control, C57BL mice were used, and after feeding a CE-2 powdered feed for 4 days, whether the male KKA$^y$ mice of the same age became obese was also examined.

The results are shown in mean±standard error. For the analysis of significance, Student's t-test was used.
2) Results The body weights of 10-week-old KKA$^y$ mice and C57BL mice were 41.4±0.7 g and 22.9±0.8 g, respectively, and the body weight of KKA$^y$ mice was found to be significantly (p<0.01) greater. Thus, the KKA$^y$ mice of this week of age were found to be in the state of obesity. The body weight gain of the KKA$^y$ mice during the test period was 1.2±0.2 g and 0.1±0.4 g, respectively, for the control group and the compound A-mixed feed group (about 6.5 mg/kg/day), and the body weight gain was significantly suppressed in the compound A-mixed feed group (p<0.05).

EXPERIMENTAL EXAMPLE 2

Effect of Compound a on Body Weight Gain Induced by PPARγ Agonist-Like Substance (Pioglitazone)
1) Test Method As the obesity rats, male Wistar fatty rats (16 week old) were used. The body weights were measured and the rats were grouped, after which a suspension of a drug in 0.5% methylcellulose solution was repeatedly and forcibly administered orally once a day for 7 consecutive days. After 24 hr from the final administration, the body weight was measured and the body weight gain was calculated. The results are shown in mean i standard error. For the analysis of significance, Student's t-test was used.
2) Results The amount of body weight gain of the control group was 24.4±2.4 g, whereas that of the PPARγ agonist-like substance administration group (pioglitazone hydrochloride: 0.5 mg/kg/day, p.o.) was 30.8±1.8 g, showing the propensity toward increase (p<0.05). The amount of body weight gain of the rats administered with a PPARγ agonist-like substance (0.5 mg/kg/day, p.o.) and compound A (1 mg/kg/day, p.o.) was 19.3±2.5 g, showing significant decrease (p<0.05) as compared to the PPARγ agonist-like substance single administration group.

EXAMPLE 1

Capsule

| | |
|---|---:|
| (1) compound A | 5 mg |
| (2) Lactose | 115 mg |
| (3) Microcrystalline cellulose | 70 mg |
| (4) Magnesium stearate | 10 mg |
| 1 capsule | 200 mg |

(1), (2), (3) and ½ of (4) are admixed and granulated. Thereto is added the remaining (4), and the total amount is sealed in a gelatin capsule.

EXAMPLE 2

Tablet

| | |
|---|---:|
| (1) compound A | 10 mg |
| (2) Lactose | 55 mg |
| (3) Cornstarch | 150 mg |
| (4) Microcrystalline cellulose | 30 mg |
| (5) Magnesium stearate | 5 mg |
| 1 tablet | 250 mg |

(1), (2), (3), ⅔ of (4) and ½ of (5) are admixed and granulated. Thereto are added the remaining (4) and (5), and the mixture is compression formed to give tablets.

EXAMPLE 3

Capsule

| | |
|---|---|
| (1) compound A | 5 mg |
| (2) Pioglitazone hydrochloride | 30 mg |
| (3) Lactose | 85 mg |
| (4) Microcrystalline cellulose | 70 mg |
| (5) Magnesium stearate | 10 mg |
| 1 capsule | 200 mg |

(1), (2), (3), (4) and ½ of (5) are admixed and granulated. Thereto is added the remaining (5), and the total amount is sealed in a gelatin capsule.

EXAMPLE 4

Tablet

| | |
|---|---|
| (1) compound A | 10 mg |
| (2) Pioglitazone hydrochloride | 30 mg |
| (3) Lactose | 25 mg |
| (4) Cornstarch | 150 mg |
| (5) Microcrystalline cellulose | 30 mg |
| (6) Magnesium stearate | 5 mg |
| 1 tablet | 250 mg |

(1), (2), (3), (4) ⅔ of (5) and ½ of (6) are admixed and granulated. Thereto are added the remaining (5) and (6), and the mixture is compression formed to give tablets.

EXAMPLE 5

Capsule

| | |
|---|---|
| (1) Candesartan cilexetil | 5 mg |
| (2) Pioglitazone hydrochloride | 30 mg |
| (3) Lactose | 85 mg |
| (4) Microcrystalline cellulose | 70 mg |
| (5) Magnesium stearate | 10 mg |
| 1 capsule | 200 mg |

(1), (2), (3), (4) and ½ of (5) are admixed and granulated. Thereto is added the remaining (5), and the total amount is sealed in a gelatin capsule.

EXAMPLE 6

Tablet

| | |
|---|---|
| (1) Candesartan cilexetil | 10 mg |
| (2) Pioglitazone hydrochloride | 30 mg |
| (3) Lactose | 25 mg |
| (4) Cornstarch | 150 mg |
| (5) Microcrystalline cellulose | 30 mg |
| (6) Magnesium stearate | 5 mg |
| 1 tablet | 250 mg |

(1), (2), (3), (4) ⅔ of (5) and ½ of (6) are admixed and granulated. Thereto are added the remaining (5) and (6), and the mixture is compression formed to give tablets.

INDUSTRIAL APPLICABILITY

The agent of the present invention shows a superior effect on the suppression of body weight gain.

For example, when a PPARγ agonist-like substance effective for the treatment of diabetes and other diseases and the like is administered, the target disease is cured, but the body weight of patients reportedly tends to increase. However, the agent of the present invention can suppress such a body weight gain in such patients.

The invention claimed is:

1. A method of inhibiting a body weight gain in a mammal comprising administering a composition consisting of an effective amount of 2-ethoxy-1-[[2'-(5-oxo-2,5-dihydro-1,2,4-oxadiazol-3-yl)biphenyl-4-yl]methyl]-1H-benzimidazole-7-carboxylic acid, a prodrug thereof or a salt thereof, an effective amount of a PPARγ agonist-like substance, and a pharmaceutically acceptable carrier in combination to the mammal.

2. The method of claim 1 wherein the PPARδ agonist-like substance is pioglitazone.

* * * * *

UNITED STATES PATENT AND TRADEMARK OFFICE
CERTIFICATE OF CORRECTION

PATENT NO. : 7,582,662 B2
APPLICATION NO. : 10/540369
DATED : September 1, 2009
INVENTOR(S) : Zen-ichi Terashita et al.

It is certified that error appears in the above-identified patent and that said Letters Patent is hereby corrected as shown below:

In claim 2, column 28, line 47, "PPARδ" should read --PPARγ--.

Signed and Sealed this

Twenty-third Day of March, 2010

David J. Kappos
*Director of the United States Patent and Trademark Office*